United States Patent
Inoue et al.

(10) Patent No.: US 10,723,686 B2
(45) Date of Patent: Jul. 28, 2020

(54) POWDERY 1,4-CYCLOHEXANEDICARBOXYLIC ACID

(71) Applicant: NEW JAPAN CHEMICAL CO., LTD., Kyoto-shi, Kyoto (JP)

(72) Inventors: Shinya Inoue, Kyoto (JP); Yoshihiro Ishibashi, Kyoto (JP); Kango Fujitani, Kyoto (JP)

(73) Assignee: NEW JAPAN CHEMICAL CO., LTD., Kyoto-shi (JP)

( * ) Notice: Subject to any disclaimer, the term of this patent is extended or adjusted under 35 U.S.C. 154(b) by 0 days.

(21) Appl. No.: 16/081,285

(22) PCT Filed: Mar. 8, 2017

(86) PCT No.: PCT/JP2017/009141
§ 371 (c)(1),
(2) Date: Aug. 30, 2018

(87) PCT Pub. No.: WO2017/154947
PCT Pub. Date: Sep. 14, 2017

(65) Prior Publication Data
US 2019/0016661 A1   Jan. 17, 2019

(30) Foreign Application Priority Data

Mar. 10, 2016   (JP) .................................. 2016-046582

(51) Int. Cl.
| | | |
|---|---|---|
| *C07C 51/36* | (2006.01) | |
| *C07C 51/43* | (2006.01) | |
| *C07C 61/09* | (2006.01) | |
| *C07C 51/09* | (2006.01) | |
| *C07C 67/303* | (2006.01) | |
| *B01J 25/02* | (2006.01) | |

(52) U.S. Cl.
CPC ............ *C07C 51/36* (2013.01); *C07C 51/09* (2013.01); *C07C 51/43* (2013.01); *C07C 61/09* (2013.01); *C07C 67/303* (2013.01); *B01J 25/02* (2013.01); *B01J 2523/821* (2013.01); *B01J 2523/847* (2013.01); *C07B 2200/13* (2013.01); *C07C 2601/14* (2017.05)

(58) Field of Classification Search
CPC ......... C07C 61/09; C07C 51/09; C07C 51/43; C07C 51/36; C07C 67/303; C07C 69/75; C07C 2601/14; B01D 45/08; B01D 46/10; B01D 50/002; B01J 2523/821; B01J 2523/847; B01J 25/02; C07B 2200/13; C07B 61/00; F24C 15/2035
See application file for complete search history.

(56) References Cited

U.S. PATENT DOCUMENTS

| | | | |
|---|---|---|---|
| 5,116,892 A * | 5/1992 | Barbee ............... | C08G 59/3209 427/185 |
| 5,118,841 A | 6/1992 | Cook et al. | |
| 5,202,475 A | 4/1993 | Cook et al. | |
| 6,291,706 B1 | 9/2001 | Sumner, Jr. et al. | |
| 2005/0014973 A1 | 1/2005 | Endou et al. | |
| 2008/0051600 A1 | 2/2008 | Endou et al. | |

FOREIGN PATENT DOCUMENTS

| | | |
|---|---|---|
| JP | 58-198439 A | 11/1983 |
| JP | 7-507041 A | 8/1995 |
| JP | 2003-128622 A | 5/2003 |
| JP | 2005-330239 A | 12/2005 |
| JP | 2005330239 * | 12/2005 |
| JP | 2010-254849 A | 11/2010 |
| WO | 93/06076 A1 | 4/1993 |
| WO | WO2016016375 * | 2/2016 |

OTHER PUBLICATIONS

JP2005330239 translated (Year: 2005).*
Davesgarden (pp. 1-7, published May 2008) (Year: 2008).*
WO2016016375 description translated (Year: 2016).*
International Search Report dated May 30, 2017, issued in counterpart application No. PCT/JP2017/009141. (2 pages).
Betnev et al., "Synthesis of Polycarboxylic Acids of Cyclohexane Series and Their Derivatives", Russian Journal of Organic Chemistry, 1999, vol. 35, No. 4, pp. 519-521 (3 pages.).

* cited by examiner

*Primary Examiner* — Yevgeny Valenrod
*Assistant Examiner* — Blaine G Doletski
(74) *Attorney, Agent, or Firm* — Westerman, Hattori, Daniels & Adrian, LLP

(57) ABSTRACT

An object of the present invention is to provide a powder of high-purity 1,4-cyclohexanedicarboxylic acid with excellent powder flowability. The invention provides a powder of high-purity 1,4-cyclohexanedicarboxylic acid having particle size distributions (volume basis) such that $D_{10}$ is within a range of 5 to 55 µm, $D_{50}$ is within a range of 40 to 200 µm, and $D_{90}$ is within a range of 170 to 800 µm; and having an aerated bulk density of 0.4 to 0.8 $g/cm^3$, a packed bulk density of 0.5 to 1.0 $g/cm^3$, and a compressibility of 10 to 23%.

7 Claims, No Drawings

POWDERY 1,4-CYCLOHEXANEDICARBOXYLIC ACID

TECHNICAL FIELD

The present invention relates to powdery 1,4-cyclohexanedicarboxylic acid.

BACKGROUND ART 1,4-Cyclohexanedicarboxylic acid is useful as a starting material of medicinal drugs, synthetic resins, synthetic fibers, dyes, etc. In particular, in view of its heat resistance, electrical properties, and optical properties, there has recently been an increasing demand for high-purity 1,4-cyclohexanedicarboxylic acid as an acid component for polyester resins for the application of optical and electronic materials.

A commonly used method for preparing 1,4-cyclohexanedicarboxylic acid comprises hydrogenating the aromatic ring of the disodium salt of terephthalic acid in an aqueous solution to give the disodium salt of 1,4-cyclohexanedicarboxylic acid, followed by precipitation by addition of an acid, such as hydrochloric acid, sulfuric acid, or the like to give 1,4-cyclohexanedicarboxylic acid (Patent Literature (PTL) 1). However, 1,4-cyclohexanedicarboxylic acid prepared by this method contains metal such as sodium from the preparation method, as well as residual acid components containing chlorine, sulfur, etc., from the precipitation by acid addition, possibly posing problems such that the polymerization degree is not easily increased in polymers obtained by using the 1,4-cyclohexanedicarboxylic acid as a starting material; and that due to the residual acid components, there are concerns about metal corrosion in devices etc., or an effect on electrical properties of the devices etc.

Other known methods comprise directly performing nuclear hydrogenation of terephthalic acid (PTL 2, PTL 3, and PTL 4). All of these methods inevitably produce impurities of monocarboxylic acids as by-products, such as cyclohexanecarboxylic acid and 4-methylcyclohexanecarboxylic acid. Furthermore, the monocarboxylic acids as impurities cannot be easily separated by recrystallization or other commonly used methods. Therefore, in terms of polymers obtained by using, as a starting material, 1,4-cyclohexanedicarboxylic acid containing these impurities, there could be problems such that the polymerization degree is not easily increased; or that there are concerns about effects on properties such as heat resistance, weather resistance, and physical strength.

Additionally, a method has also been proposed for obtaining 1,4-cyclohexanedicarboxylic acid by subjecting dialkyl terephthalate to nuclear hydrogenation, and subjecting the resulting dialkyl 1,4-cyclohexanedicarboxylate to a hydrolysis reaction in an aqueous solution in the presence of an acid catalyst. In this method, at the time of hydrolysis, water is continuously or intermittently added to the reaction system while water and a by-product alcohol produced during the hydrolysis reaction are continuously evaporated out of the reaction system (PTL 5).

As described above, in general, for organic compounds, increasing purity and reducing the content of impurities could be primary problems to be solved. In terms of an organic compound in the form of a powder, an industrially important problem is whether the powder handleability is satisfactory. The powder handleability is mainly evaluated based on powder flowability and floodability. Depending on the degree of the powder flowability and floodability, installation of corresponding mechanical devices or an improvement in working environment etc. could be required, which is economically disadvantageous. Solving such problems is often not easy because even organic compounds with the same chemical structure have different powder properties due to the effects of, for example, their production history, storage history, and characteristic properties specific to the substance (stickiness, adhesion, etc.). That is, one of the factors that makes it more difficult to improve the powder handleability lies in the difficulty in identifying the cause of the effect on powder properties.

CITATION LIST

Patent Literature

PTL 1: WO93/06076
PTL 2: JPS58-198439A
PTL 3: U.S. Pat. No. 6,291,706
PTL 4: JP2003-128622A
PTL 5: JP2005-330239A

SUMMARY OF INVENTION

Technical Problem

An object of the present invention is to provide a powder of 1,4-cyclohexanedicarboxylic acid with excellent powder flowability.

Solution to Problem

The present invention provides powdery 1,4-cyclohexanedicarboxylic acid and a production method thereof, as summarized in the items below.

Item 1: Powdery 1,4-cyclohexanedicarboxylic acid having:
particle size distributions (volume basis) such that $D_{10}$ is within a range of 5 to 55 µm, $D_{50}$ is within a range of 40 to 200 µm, and $D_{90}$ is within a range of 170 to 800 µm;
an aerated bulk density of 0.4 to 0.8 g/cm$^3$;
a packed bulk density of 0.5 to 1.0 g/cm$^3$; and
a compressibility of 10 to 23%.

Item 2: The powdery 1,4-cyclohexanedicarboxylic acid according to Item 1,
wherein the cis:trans ratio in the 1,4-cyclohexanedicarboxylic acid is 50:50 to 90:10.

Item 3: The powdery 1,4-cyclohexanedicarboxylic acid according to Item 1 or 2, containing dialkyl (C1-C4) terephthalate, monoalkyl (C1-C4) terephthalate, and terephthalic acid in a total amount of 0.2% or less in the powdery 1,4-cyclohexanedicarboxylic acid.

Item 4: The powdery 1,4-cyclohexanedicarboxylic acid according to any one of Items 1 to 3,
wherein the powdery 1,4-cyclohexanedicarboxylic acid satisfies at least one member selected from the group consisting of the following (a) to (e):
(a) containing alkyl (C1-C4) cyclohexanecarboxylate in an amount of 0.1% or less;
(b) containing cyclohexanecarboxylic acid in an amount of 0.1% or less;
(c) containing alkyl (C1-C4) 4-methylcyclohexanecarboxylate in an amount of 0.1% or less;
(d) containing 4-methylcyclohexanecarboxylic acid in an amount of 0.3% or less; and (e) containing monoalkyl (C1-C4) 1,4-cyclohexanedicarboxylate in an amount of 0.5% or less,
and also satisfies at least one member selected from the group consisting of the following (i) to (iii):
(i) containing one or more alkali metals in an amount of 20 ppm or less (weight basis);
(ii) containing water in an amount of 0.1 wt % or less; and
(iii) having a color number (Hazen) of 50 or less.

Item 5: The powdery 1,4-cyclohexanedicarboxylic acid according to any one of Items 1 to 4, having an angle of repose of 46 degrees or less, and a dispersion percentage of 20% or more.

Item 6: A method for producing powdery 1,4-cyclohexanedicarboxylic acid,
the method comprising the steps of:
(1) subjecting dialkyl (C1-C4) terephthalate to nuclear hydrogenation to obtain dialkyl (C1-C4) 1,4-cyclohexanedicarboxylate;
(2) hydrolyzing the dialkyl (C1-C4) 1,4-cyclohexanedicarboxylate obtained in step (1) in the presence of an acid catalyst in the presence of water or a water-containing solvent to obtain 1,4-cyclohexanedicarboxylic acid;
(3) crystallizing the 1,4-cyclohexanedicarboxylic acid obtained in step (2);
(4) subjecting the crystals of the 1,4-cyclohexanedicarboxylic acid obtained in step (3) to solid-liquid separation; and
(5) drying, drying and granulating, or drying and crushing wet crystals of the 1,4-cyclohexanedicarboxylic acid obtained in step (4); and optionally
(6) classifying a powder of the 1,4-cyclohexanedicarboxylic acid obtained in step (5).

Item 7: The production method according to Item 6, wherein the step of drying the wet crystals in step (5) is a step of drying the wet crystals while stirring.

Item 8: The production method according to Item 6 or 7, wherein the hydrolysis reaction in step (2) is performed by continuously or intermittently adding water to the reaction system at a liquid space velocity of within a range of 0.05 to 0.5/h on a reaction solution volume basis.

Item 9: Powdery 1,4-cyclohexanedicarboxylic acid produced by the production method of any one of Items 6 to 8.

Item 10: A method for using the powdery 1,4-cyclohexanedicarboxylic acid of any one of Items 1 to 5 and 9 as a polymer starting material.

Item 11: A method for producing a polymer using the powdery 1,4-cyclohexanedicarboxylic acid of any one of Items 1 to 5 and 9.

Item 12: A method for producing a polyester or a polyamide by reacting the powdery 1,4-cyclohexanedicarboxylic acid of any one of Items 1 to 5 and 9 with an alcohol or an amine.

Advantageous Effects of Invention

The powdery 1,4-cyclohexanedicarboxylic acid according to the present invention has excellent powder flowability. Further, the powdery 1,4-cyclohexanedicarboxylic acid according to Items 3 to 7 above is of higher purity.

DESCRIPTION OF EMBODIMENTS

The 1,4-cyclohexanedicarboxylic acid according to the present invention is in the form of a powder. It is recommended that the particle size distributions (on a volume basis) of the powdery 1,4-cyclohexanedicarboxylic acid be such that $D_{10}$ is within a range of 5 to 55 μm, $D_{50}$ is within a range of 40 to 200 μm, and $D_{90}$ is within a range of 170 to 800 μm; preferably such that $D_{10}$ is within a range of 5 to 55 μm, $D_{50}$ is within a range of 40 to 200 μm, and $D_{90}$ is within a range of 170 to 600 μm; and more preferably such that $D_{10}$ is within a range of 10 to 50 μm, $D_{50}$ is within a range of 45 to 130 μm, and $D_{90}$ is within a range of 175 to 500 μm. It is further recommended that the particle size distributions be still more preferably such that $D_{10}$ is within a range of 13 to 45 μm, $D_{50}$ is within a range of 50 to 100 μm, and $D_{90}$ is within a range of 180 to 350 μm; and particularly preferably such that $D_{10}$ is within a range of 15 to 45 μm, $D_{50}$ is within a range of 50 to 100 μm, and $D_{90}$ is within a range of 180 to 300 μm.

The particle size distribution values ($D_{10}$, $D_{50}$, $D_{90}$, and average particle size) according to the present invention are as measured by a dry process using the laser diffraction-light scattering method. For devices used in this measurement method, commercially available measurement devices marketed by MicrotracBEL Corp., Malvern Instruments Ltd., Beckman Coulter, Inc., and Shimazu Corporation, Inc., which are of high accuracy, can be effectively used for analysis in the present invention.

The values of particle size distributions ($D_{10}$, $D_{50}$, $D_{90}$, and average particle size) are arithmetic mean values of each particle size distribution ($D_{10}$, $D_{50}$, $D_{90}$, or average particle size) measured with respect to each sample; two or more samples are taken (n≥2) with respect to the same powder.

The bulk densities of powdery 1,4-cyclohexanedicarboxylic acid refer to an aerated bulk density and a packed bulk density. The aerated bulk density is also called a loose bulk density, and represents an apparent density obtained by filling a powder into a graduated cylinder of a certain volume without applying vibration. The packed bulk density is also called close-packed bulk density, and is obtained, after the measurement of the aerated bulk density, by tapping the cylinder containing the powder a certain number of times, and filling the powder again. Compressibility (%) can be calculated based on the obtained aerated bulk density and packed bulk density. The compressibility represents the degree of bulk volume reduction, and is one of the indices of powder flowability. In general, a greater compressibility represents poor powder flowability, and a smaller compressibility represents more excellent powder flowability.

The powdery 1,4-cyclohexanedicarboxylic acid according to the present invention usually has an aerated bulk density of 0.4 to 0.8 g/cm$^3$, a packed bulk density of 0.5 to 1.0 g/cm$^3$, and a compressibility of 10 to 23%; preferably an aerated bulk density of 0.5 to 0.75 g/cm$^3$, a packed bulk density of 0.6 to 0.95 g/cm$^3$, and a compressibility of 10 to 22%; and more preferably an aerated bulk density of 0.6 to 0.7 g/cm$^3$, a packed bulk density of 0.7 to 0.85 g/cm$^3$, and a compressibility of 10 to 21%.

When the particle size distributions, the bulk densities, and the compressibility are within the above ranges, it is possible to obtain 1,4-cyclohexanedicarboxylic acid with excellent powder flowability. If the powder is finer and is outside the above ranges, the powder flowability tends to become less satisfactory. In contrast, if the powder is larger and is outside the above ranges, impurities are easily incorporated, and the purity tends to decrease.

The following are preferable combination of embodiments.

When $D_{10}$ is within a range of 5 to 55 μm, $D_{50}$ is within a range of 40 to 200 μm, and $D_{90}$ is within a range of 170 to 800 μm, the aerated bulk density is 0.4 to 0.8 g/cm$^3$, and the packed bulk density is 0.5 to 1.0 g/cm$^3$.

When $D_{10}$ is within a range of 5 to 55 μm, $D_{50}$ is within a range of 40 to 200 μm, and $D_{90}$ is within a range of 170 to 600 µm, the aerated bulk density is 0.4 to 0.8 g/cm³, and the packed bulk density is 0.5 to 1.0 g/cm³.

When $D_{10}$ is within a range of 10 to 50 µm, $D_{50}$ is within a range of 45 to 130 µm, and $D_{90}$ is within a range of 175 to 500 µm, the aerated bulk density is 0.4 to 0.8 g/cm³, and the packed bulk density is 0.5 to 1.0 g/cm³.

When $D_{10}$ is within a range of 13 to 45 µm, $D_{50}$ is within a range of 50 to 100 µm, and $D_{90}$ is within a range of 180 to 350 µm, the aerated bulk density is 0.4 to 0.8 g/cm³, and the packed bulk density is 0.5 to 1.0 g/cm³.

When $D_{10}$ is within a range of 15 to 45 µm, $D_{50}$ is within a range of 50 to 100 µm, and $D_{90}$ is within a range of 180 to 300 µm, the aerated bulk density is 0.4 to 0.8 g/cm³, and the packed bulk density is 0.5 to 1.0 g/cm³.

When $D_{10}$ is within a range of 5 to 55 µm, $D_{50}$ is within a range of 40 to 200 µm, and $D_{90}$ is within a range of 170 to 800 µm, the aerated bulk density is 0.5 to 0.75 g/cm³, and the packed bulk density is 0.6 to 0.95 g/cm³.

When $D_{10}$ is within a range of 5 to 55 µm, $D_{50}$ is within a range of 40 to 200 µm, and $D_{90}$ is within a range of 170 to 600 µm, the aerated bulk density is 0.5 to 0.75 g/cm³, and the packed bulk density is 0.6 to 0.95 g/cm³.

When $D_{10}$ is within a range of 10 to 50 µm, $D_{50}$ is within a range of 45 to 130 µm, and $D_{90}$ is within a range of 175 to 500 µm, the aerated bulk density is 0.5 to 0.75 g/cm³, and the packed bulk density is 0.6 to 0.95 g/cm³.

When $D_{10}$ is within a range of 13 to 45 µm, $D_{50}$ is within a range of 50 to 100 µm, and $D_{90}$ is within a range of 180 to 350 µm, the aerated bulk density is 0.5 to 0.75 g/cm³, and the packed bulk density is 0.6 to 0.95 g/cm³.

When $D_{10}$ is within a range of 15 to 45 µm, $D_{50}$ is within a range of 50 to 100 µm, and $D_{90}$ is within a range of 180 to 300 µm, the aerated bulk density is 0.5 to 0.75 g/cm³, and the packed bulk density is 0.6 to 0.95 g/cm³.

When $D_{10}$ is within a range of 5 to 55 µm, $D_{50}$ is within a range of 40 to 200 µm, and $D_{90}$ is within a range of 170 to 800 µm, the aerated bulk density is 0.6 to 0.7 g/cm³, and the packed bulk density is 0.7 to 0.85 g/cm³.

When $D_{10}$ is within a range of 5 to 55 µm, $D_{50}$ is within a range of 40 to 200 µm, and $D_{90}$ is within a range of 170 to 600 µm, the aerated bulk density is 0.6 to 0.7 g/cm³, and the packed bulk density is 0.7 to 0.85 g/cm³.

When $D_{10}$ is within a range of 10 to 50 µm, $D_{50}$ is within a range of 45 to 130 µm, and $D_{90}$ is within a range of 175 to 500 µm, the aerated bulk density is 0.6 to 0.7 g/cm³, and the packed bulk density is 0.7 to 0.85 g/cm³.

When $D_{10}$ is within a range of 13 to 45 µm, $D_{50}$ is within a range of 50 to 100 µm, and $D_{90}$ is within a range of 180 to 350 µm, the aerated bulk density is 0.6 to 0.7 g/cm³, and the packed bulk density is 0.7 to 0.85 g/cm³.

When $D_{10}$ is within a range of 15 to 45 µm, $D_{50}$ is within a range of 50 to 100 µm, and $D_{90}$ is within a range of 180 to 300 µm, the aerated bulk density is 0.6 to 0.7 g/cm³, and the packed bulk density is 0.7 to 0.85 g/cm³.

In particular, to achieve excellent powder flowability of powdery 1,4-cyclohexanedicarboxylic acid, the relationship between the compressibility and the particle size distribution, $D_{50}$, is important. Specifically, it is recommended that the compressibility be within a range of 10 to 23%, and $D_{50}$ be within a range of 40 to 200 µm; preferably that the compressibility be within a range of 10 to 22%, and $D_{50}$ be within a range of 45 to 130 µm; and more preferably that the compressibility be within a range of 10 to 21%, and $D_{50}$ be within a range of 50 to 100 µm.

The powdery 1,4-cyclohexanedicarboxylic acid usually has an average particle size of 35 to 220 µm, preferably 40 to 200 µm, and more preferably 45 to 130 µm.

It is recommended that the angle of repose, which is one of the indices of powder flowability, be preferably 46 degrees or less, more preferably 45 degrees or less, and particularly preferably 40 degrees or less. The angle of repose usually represents an angle, relative to the horizontal plane, of the generatrix, i.e., the slope of the conical pile produced when a powder is gently dropped onto a horizontal surface through a funnel or the like. The angle of repose is determined by the size, roundness, and shape of particles.

It is recommended that the dispersion percentage, which is one of the indices of floodability, be preferably 20% or more, and more preferably 25% or more. The dispersion percentage is usually calculated by allowing a certain amount of a powder to naturally fall down from a certain height, and weighing the amount of the powder remaining, without scattering, on a table placed at the point where the powder falls down.

The angle of repose and the dispersion percentage can be measured using known measurement methods and powder characteristics testers. The measurement may be performed by using, for example, Multi Tester MT-01 or MT-02 produced by Seishin Enterprise Co., Ltd., and a powder tester PT-X produced by Hosokawa Micron Ltd.

The powdery 1,4-cyclohexanedicarboxylic acid according to the present invention may sometimes contain dialkyl (C1-C4) terephthalate, monoalkyl (C1-C4) terephthalate, or terephthalic acid as impurities, according to the production method or production conditions. It is recommended that the total content of these impurities in the powdery 1,4-cyclohexanedicarboxylic acid be usually 0.2% or less, preferably 0.1% or less, and particularly preferably 0.001 to 0.05%. Such 1,4-cyclohexanedicarboxylic acid of high purity is suitably used in various applications that require high performance.

In this specification, the term "alkyl (C1-C4)" refers to a C1-C4 alkyl group (i.e., methyl, ethyl, n-propyl, isopropyl, n-butyl, isobutyl, sec-butyl, or tert-butyl). The term "dialkyl (C1-C4)" represents two C1-4 alkyl groups, and these two C1-4 alkyl groups may be identical or different.

The powdery 1,4-cyclohexanedicarboxylic acid according to the present invention may sometimes contain the following impurities (a) to (e), according to the production method or production conditions.
(a) Alkyl (C1-C4) cyclohexanecarboxylate,
(b) Cyclohexanecarboxylic acid,
(c) Alkyl (C1-C4) 4-methylcyclohexanecarboxylate,
(d) 4-Methylcyclohexanecarboxylic acid, and
(e) Monoalkyl (C1-C4) 1,4-cyclohexanedicarboxylate.

The content of the impurities (a) to (e) in the powdery 1,4-cyclohexanedicarboxylic acid is, for example, as follows.
(a) the alkyl (C1-C4) cyclohexanecarboxylate content is usually 0.1% or less (preferably 0.05% or less, and in particular 0.001 to 0.05%),
(b) the cyclohexanecarboxylic acid content is usually 0.3% or less (preferably 0.1% or less, and in particular 0.001 to 0.1%),
(c) the alkyl (C1-C4) 4-methylcyclohexanecarboxylate content is usually 0.1% or less (more preferably 0.05% or less, and in particular 0.001 to 0.05%),
(d) the 4-methylcyclohexanecarboxylic acid content is usually 0.3% or less (preferably 0.2% or less, and in particular 0.001 to 0.2%), and
(e) the monoalkyl (C1-C4) 1,4-cyclohexanedicarboxylate content is usually 0.5% or less (preferably 0.2% or less, and particularly preferably 0.001 to 0.2%).

The powdery 1,4-cyclohexanedicarboxylic acid desirably satisfies at least one member (preferably two, more preferably three, still more preferably four, and particularly preferably all of the members) selected from the group consisting of the above (a) to (e).

The powdery 1,4-cyclohexanedicarboxylic acid according to the present invention preferably comprises high-purity 1,4-cyclohexanedicarboxylic acid. The content (purity) of 1,4-cyclohexanedicarboxylic acid in the powder is usually 98% or more, preferably 98.5% or more, and more preferably 99% or more.

In this specification, the expression "%" in terms of the purity of 1,4-cyclohexanedicarboxylic acid and the contents of impurities represents "a simple area percentage" obtained by gas chromatographic analysis.

When the impurity content above is defined only with the upper limit, the lower limit is 0%, which represents "below the detection limit" (hereinafter may also be expressed as "about a trace amount") in the gas chromatographic analysis described below. There are acceptable ranges in terms of the contents of impurities according to the applications, or according to the quality control in an industrial-scale production. In view of both of these viewpoints, more preferable ranges can be determined.

The impurities above result from the method for producing 1,4-cyclohexanedicarboxylic acid, comprising subjecting dialkyl terephthalate to nuclear hydrogenation, followed by hydrolysis. The use of 1,4-cyclohexanedicarboxylic acid that contains a large amount of these impurities may make it difficult to increase the degree of polymerization of a polymer, or may cause an adverse effect on properties, such as heat resistance, weather resistance, and physical strength. In the present invention, the above impurities can be minimized by using, for example, the production method of Items 6 to 8 above.

Further, it is recommended that the powdery 1,4-cyclohexanedicarboxylic acid have the following properties (i) to (iii):
(i) the alkali metal content (weight basis) is usually 20 ppm or less (preferably 10 ppm or less),
(ii) the water content is usually 0.1 wt % or less (preferably 0.06 wt % or less, and particular preferably 0.04 wt % or less), and
(iii) the color number (Hazen) is usually 50 or less (preferably 30 or less, and particular preferably 20 or less).

The powdery 1,4-cyclohexanedicarboxylic acid desirably satisfies at least one property (preferably two, and more preferably three properties) selected from the group consisting of the above (i) to (iii) to achieve high purity and reduce coloration.

The values of impurities in the properties (i) and (ii) above are defined only with the upper limits; the lower limits for (i) and (ii) are respectively 0 ppm and 0 wt %, which represent "below the detection limit" (hereinafter may also be expressed as "about a trace amount") in the metal analysis or water content measurement (Karl Fischer titration) described below. The value in (i) (alkali metal content) usually refers to the total content of sodium and potassium, but substantially refers to the sodium content.

The color number (Hazen) (the value in (iii)) is also defined using only the upper limit; the lower limit is 0.

According to the applications, the values in the properties (i) to (iii) may cause effects similar to those of the impurities described above. Moreover, the water content in (ii) certainly affects the purity, and also affects the powder flowability. The amounts in relation to the values in (i) and (ii) are both on a weight basis.

1,4-Cyclohexanedicarboxylic acid has geometrical isomers, i.e., cis (cis form) and trans (trans form) isomers. In the present invention, it is recommended that the cis:trans ratio in 1,4-cyclohexanedicarboxylic acid be preferably such that cis:trans=50:50 to 90:10, and more preferably such that cis:trans=65:35 to 85:15.

The cis:trans ratio in 1,4-cyclohexanedicarboxylic acid in this specification is represented by the ratio of "simple area percentages" obtained in the gas chromatographic analysis.

As used in this specification and the claims, the "powder" of the powdery 1,4-cyclohexanedicarboxylic acid according to the present invention is a collective term of powders, granules, grains, and fine particles. The powder is usually formed as an aggregate of crystals in the form of needles, plates, columns, or the like, or irregularly shaped crystals.

The following are examples of methods for producing the 1,4-cyclohexanedicarboxylic acid according to the present invention.

More specifically, a recommended production method comprises:
(1) subjecting dialkyl (C1-C4) terephthalate to nuclear hydrogenation to obtain dialkyl (C1-C4) 1,4-cyclohexanedicarboxylate;
(2) hydrolyzing the dialkyl (C1-C4) 1,4-cyclohexanedicarboxylate in the presence of an acid catalyst in the presence of water or a water-containing solvent to obtain 1,4-cyclohexanedicarboxylic acid;
(3) crystallizing the 1,4-cyclohexanedicarboxylic acid;
(4) subjecting the crystals of the 1,4-cyclohexanedicarboxylic acid to solid-liquid separation; and
(5) drying the wet crystals of the 1,4-cyclohexanedicarboxylic acid obtained in step (4), drying and granulating the wet crystals of the 1,4-cyclohexanedicarboxylic acid obtained in step (4), or drying and crushing the wet crystals of the 1,4-cyclohexanedicarboxylic acid obtained in step (4).

The production method may further optionally comprise, according to the purpose of use, (6) classifying a powder of the 1,4-cyclohexanedicarboxylic acid obtained in step (5).

The following more specifically describes the production method in accordance with the above steps.

Step (1):

Nuclear hydrogenation of the aromatic ring of dialkyl terephthalate, usually in the presence of a nickel catalyst, a ruthenium catalyst, a palladium catalyst, a platinum catalyst, or a rhodium catalyst (particularly preferably a ruthenium catalyst), enables the preparation of dialkyl (C1-C4) 1,4-cyclohexanedicarboxylate. Examples of such production methods include the methods disclosed in JPS54-163554A, JPH06-192146A, JPH07-149694A, WO 98/00383, JP2000-1447A, and the like.

Of these, the method for producing dialkyl 1,4-cyclohexanedicarboxylate disclosed in JP2000-1447A is preferable since the resulting product is of a purity of 98% or higher, and a small amount of by-product impurities, such as alkyl cyclohexanecarboxylate and alkyl 4-methylcyclohexanecarboxylate, are produced.

Specific examples of the dialkyl (C1-C4) terephthalate according to the present invention include dimethyl terephthalate, diethyl terephthalate, di-n-propyl terephthalate, diisopropyl terephthalate, di-n-butyl terephthalate, and the like, with dimethyl terephthalate being preferable.

Step (2):

Specific examples of the acid catalyst used for hydrolyzing the dialkyl (C1-C4) 1,4-cyclohexanedicarboxylate produced by the nucleus hydrogenation reaction of dialkyl terephthalate include mineral acids, such as hydrochloric acid, sulfuric acid, and nitric acid; organic acids, such as methanesulfonic acid and p-toluenesulfonic acid; heteropolyacids, such as phosphotungstic acid; solid acids, such as sulfonic acid type-cation exchange resin; and the like, with hydrochloric acid, sulfuric acid, methanesulfonic acid, and p-toluenesulfonic acid being preferable.

It is recommended that the amount of the acid catalyst used be usually about 0.5 to 10 wt %, and preferably about 1 to 7 wt %, relative to dialkyl (C1-C4) 1,4-cyclohexanedicarboxylate as a starting material. As a reaction solvent of the hydrolysis reaction, water or a water-containing solvent (preferably water) is usually used. Specific examples of the water include tap water, ion exchanged water, reverse osmosis membrane-treated water, ultrafiltration membrane-treated water, distilled water, and the like. Of these, purified water, such as ion exchanged water and distilled water, is preferable to prevent metal incorporation.

For the amount of water used in the hydrolysis reaction, it is recommended that the concentration of dialkyl (C1-C4) 1,4-cyclohexanedicarboxylate as a substrate be within a range of 2 to 50 wt %, and preferably 10 to 40 wt %. It is recommended that the hydrolysis reaction temperature under ordinary pressure (atmospheric pressure) be usually within a range of 90 to 100° C., and preferably 98 to 100° C. The reaction time is usually within a range of 1 to 15 hours. In a hydrolysis reaction, which is an equilibrium reaction, it is important for the equilibrium to be biased toward the 1,4-cyclohexanedicarboxylic acid production side (hydrolysis side). An example of this method comprises removing water and the by-product alcohol produced during the hydrolysis reaction by continuously distilling them off from the reaction system. When this method is performed, it is preferable to continuously or intermittently add, to the reaction system, water with the same weight as that of the distilled water or the distillate of water and by-product alcohol, simultaneously with the removal operation. In this removal operation, impurities, such as alkyl cyclohexanecarboxylate and alkyl 4-methylcyclohexanecarboxylate, which are produced as by-products in the nucleus hydrogenation reaction, can also be removed from the reaction system, together with the distilled water or distilled mixture of water and the alcohol. Thus, this removal operation is considered to be a preferable embodiment in terms of achieving high purity.

The method for adding water is not particularly limited. It is preferable to add water after being heated to a predetermined temperature to avoid lowering the reaction temperature. It is recommended that the water be continuously or intermittently added to the reaction system at a liquid space velocity on a reaction solution volume basis of usually within a range of 0.05 to 0.5/h, preferably 0.05 to 0.4/h, more preferably 0.05 to 0.3/h, and still more preferably 0.1 to 0.25. The range of 0.05 to 0.2/h, and further the range of 0.1 to 0.15/h, may also be selected according to the reaction conditions.

Step (1) and step (2) may be suitably performed with reference to, for example, PTL 5 (JP2005-330239A).

Step (3):

In the crystallization step after the hydrolysis step, the obtained hydrolysis reaction solution is cooled to usually 40° C. or lower, preferably to 20° C. or lower, and further more preferably to 0 to 15° C. to crystallize 1,4-cyclohexanedicarboxylic acid. At this time, it is important to suitably analyze and determine, according to the desirable purpose, the step conditions such as cooling rate, slurry concentration, and stirring operation (stirring speed, Reynolds number, stirring blade shape, etc.), in consideration of the effects on the crystals or crystallization (including the effects on, for example, particle size distributions, crystal structures, and inclusion of impurities). For example, in terms of the cooling rate, if cooling is performed slowly, large crystals are likely to be obtained. Since the cooling rate affects the properties and production efficiency of the powder according to the present invention, the step conditions are suitably analyzed and determined.

Step (4):

The solid-liquid separation step is not particularly limited as long as a solid-liquid separation operation can be performed. The slurry obtained by the crystallization step is separated into the wet crystals of 1,4-cyclohexanedicarboxylic acid and the crystallization mother liquid.

Any solid-liquid separator may be used as long as it has general-purpose separation functions. For example, batch-type separators, such as a vacuum filter, a press filter, or a centrifugal filter, may be used. These solid-liquid separators are preferably provided with a device that supplies rinse water for washing the acid catalyst and impurities adhering to the surface of wet crystals.

The amount of the rinse water used is preferably 30 to 200 wt %, relative to the wet crystals of 1,4-cyclohexanedicarboxylic acid. If the amount is smaller than this range, impurities and the acid catalyst would easily remain. If the amount is larger than this range, waste water would increase, deteriorating the production efficiency.

The crystallization mother liquid is obtained as a filtrate of the solid-liquid separator. This crystallization mother liquid contains an acid catalyst and 1,4-cyclohexanedicarboxylic acid that was not crystallized in the crystallization step, and is desirably reused in the hydrolysis reaction from an economic viewpoint. In reusing, impurities originating from alkyl 1,4-cyclohexanedicarboxylate as the reaction starting material may accumulate, possibly reducing the purity of the 1,4-cyclohexanedicarboxylic acid as a final product. As long as the reduction in purity is within a tolerable range, reusing can be performed repeatedly.

Step (5):

The separated wet crystals of 1,4-cyclohexanedicarboxylic acid are dried, or dried and granulated or crushed (or cracked), to give a dry solid (powder). Specifically, the wet crystals are dried, and optionally granulated and/or crushed (cracked) to obtain a powder.

For drying conditions, the technique and devices are suitably selected usually in view of the purpose of use, treatment efficiency, etc. Examples of a suitable drying step include drying the wet crystals of 1,4-cyclohexanedicarboxylic acid while stirring. For drying, a stirring-type dryer may be used. When the wet crystals are dried while being allowed to stand, the wet crystals are dissolved due to their water content, allowing the crystals to aggregate, or causing blocking. To avoid this, it is recommended that the wet crystals be dried while being stirred. In this manner, a powder of 1,4-cyclohexanedicarboxylic acid with excellent powder flowability can be prepared.

It is recommended that the dry solid (powder) be dried so as to eventually achieve a water content of preferably 0.1 wt % or less, more preferably 0.06 wt % or less, and particularly 0.04 wt % or less, on the basis of the weight of the dry solid (powder).

Additionally, a granulation operation can be performed simultaneously with the drying operation or after the drying operation. To perform the granulation operation, a granulator and granulation conditions may be suitably selected, according to the purpose of use. Examples of stirring and mixing granulation include a method for growing particles by subjecting the wet crystals to the action of shear, rolling motion, compaction, etc., by means of rotation of stirring blades; a method for subjecting crystals to rolling motion and granulation in a fluid bed; and a method for subjecting a dry solid (powder) to granulation to obtain granules, fine particles, or the like by a compression molding machine etc.

Further, it is possible to perform a crushing operation after the drying operation. The crushing may be, for example, fine crushing (nearly about 10 to 150 µm), medium crushing (nearly about 300 to 500 µm), or coarse crushing or cracking (nearly about 1 to 10 mm). To perform the crushing operation, a crushing device and/or crushing conditions are suitably selected or combined to agree with the object of the present invention. Examples include a method of performing coarse crushing or medium crushing mainly using compression force or impact force, and a method of performing fine crushing mainly using shearing force and frictional force, in addition to compression force or impact force.

Step (5) above affects the powder flowability. Thus, in this step, it is important to adjust the step conditions such that the particle size distributions, the bulk densities, and the compressibility are within the ranges of the present invention. The step conditions may be suitably adjusted, based on the above procedures. Although the adjustment to be within the above ranges can also be performed in the classification step (6) described below, it is economically more advantageous to perform a smaller number of preparation steps.

Step (6):

The dry solid (powder) may optionally be classified. To perform the classification step, a classifier and classification conditions are suitably selected and used according to the purpose of use. Examples include a method that uses a screen (sieving and screen classification), and a method of classification with the use of a wind force using a specific gravity difference (air classification).

The thus-obtained powdery 1,4-cyclohexanedicarboxylic acid according to the present invention is 1,4-cyclohexanedicarboxylic acid with excellent powder flowability, and is high-purity 1,4-cyclohexanedicarboxylic acid with a reduced amount of impurities and excellent physical properties.

The powdery 1,4-cyclohexanedicarboxylic acid according to the present invention is of high purity, has excellent powder flowability, and contains a reduced amount of impurities. This powdery 1,4-cyclohexanedicarboxylic acid may be used as a starting material for producing, for example, polymers, such as polyesters and polyamides. Specifically, an ester (e.g., a polyester) or an amide (e.g., a polyamide) may be produced by reacting the powdery 1,4-cyclohexanedicarboxylic acid with an alcohol (e.g., diol or polyol) or an amine (e.g., diamine or polyamine). In the reaction steps above, the handleability significantly improves, and the obtained ester or amide is of extremely high purity. Thus, the powdery 1,4-cyclohexanedicarboxylic acid according to the present invention may be used as a starting material of various useful polymers, such as medicinal drugs, synthetic resins, synthetic fibers, and dyes.

EXAMPLES

The present invention is described below in more detail with reference to Examples. However, the present invention is not limited to these Examples. The evaluation methods used in the Example are as follows.

1) Particle Size Distribution

The particle size distributions (volume basis) were measured by the laser diffraction-light scattering method (device: "Mastersizer 3000," produced by Malvern Instruments Ltd.), based on a dry process, and the $D_{10}$, $D_{50}$, $D_{90}$, and the average particle size were determined. The "$D_{10}$" represents the particle size corresponding to the 10% cumulative volume, "$D_{50}$" represents the particle size (median size) corresponding to the 50% cumulative volume, and "$D_{90}$" represents the particle size corresponding to the 90% cumulative volume.

2) Angle of Repose and Dispersion Percentage

The angle of repose and dispersion percentage were measured with a powder characteristics tester (a PT-X powder tester, produced by Hosokawa Micron Ltd.).

3) Bulk Density and Compressibility

Bulk Density

The weight per unit volume of a sample is measured, and the resulting value is considered as an apparent density. A graduated cylinder is placed on an electronic scale, and the scale is reset to zero. The sample is placed in the graduated cylinder up to the scale of 100 ml, and the weight is accurately measured to the nearest 0.1 g (A g). The apparent density at this time is referred to as the "aerated bulk density (g/cm³)."

Thereafter, the graduated cylinder containing the sample is dropped onto a rubber sheet (impact table; about 3-mm thickness) 50 times from the height of 5 cm, and the scale (B cm³) of the graduated cylinder is read. The apparent density at this time is referred to as the "packed bulk density (g/cm³)."

$$\text{Aerated bulk density (g/cm}^3\text{)}=A/100 \quad (1)$$

$$\text{Packed bulk density (g/cm}^3\text{)}=A/B \quad (2)$$

From the viewpoint of powder flowability, it is recommended that the aerated bulk density be 0.4 to 0.8 g/cm³, and the packed bulk density be 0.5 to 1.0 g/cm³.

Compressibility

The compressibility (%) was calculated using the following formula (3), based on the measured values of the aerated bulk density and packed bulk density.

$$\text{Compressibility (\%)}=\{(\text{packed bulk density}-\text{aerated bulk density})/\text{packed bulk density}\}\times 100 \quad (3)$$

From the viewpoint of powder flowability, it is recommended that the compressibility be 23% or less.

4) Gas Chromatography Analysis

Device: GC-2010 (produced by Shimazu Corporation)
Detector: FID 325° C.
Column: TC-5 (30 m×0.25 mmφ)
Injection temperature: 300° C.
Column temperature: from 100° C. (maintained 2 min) to 320° C., 10° C./min In the Examples, the expression "%" in terms of the purity of 1,4-cyclohexanedicarboxylic acid and the amounts of impurities represents "a simple area percentage" obtained by gas chromatographic analysis. The "simple area percentage" simply refers to the percentage of each peak area, relative to the total peak areas detected in the gas chromatogram, without correction. The measurement sample was pretreated with a silylating agent, N,O-bis(trimethylsilyl)trifluoroacetamide (BSTFA). The cis:trans ratio in 1,4-cyclohexanedicarboxylic acid is represented by the ratio of the "simple area percentages" by the gas chromatographic analysis.

5) Melting Point Measurement (Differential Scanning Calorimeter)

Device: DSC6220 (produced by Seiko Instruments, Inc.)
Equipment name: Electrical sample sealer (produced by Epolead Service Inc.)

Temperature elevation rate: from 50° C. to 200° C., 10° C./min

The temperatures referred to in the Examples are endothermic peak top temperatures.

6) Metal Analysis (ICP Emission Spectrochemical Analysis)
Device: iCAP6500Duo (produced by Thermo Fisher Scientific)

Pretreatment was performed based on microwave digestion techniques, and metal analysis was performed. For pretreatment, 0.3 g of a sample and 6 ml of special-grade nitric acid were digested in a microwave digestion apparatus using a Multiwave PRO (produced by Anton Paar), and the total amount was adjusted to 15 g with distilled water. Thereafter, metal analysis was performed with an ICP emission spectrophotometer.

As for the metal contents (on a weight basis), it is recommended that the sodium content be 10 ppm or less, and the iron content be 0.3 ppm or less.

7) Water Content

The water content (wt %) was measured by Karl Fischer titration.
Water measurement device: AQV-2100 (produced by Hiranuma Sangyo Co., Ltd.)
Titrant: HYDRANAL-Composite 5K (produced by Sigma-Aldrich)
Solvent: 150 ml of methanol (super-dehydrated), 50 ml of ethylene glycol, and 300 ml of chloroform One gram of a sample weighed on a weighing paper was introduced into the solvent, and the mixture was dissolved under stirring for 1 minute, followed by measurement of the water content.

8) Color Number (Hazen)
Device: Transparent color number measurement device (OME-2000 measurement device for petroleum products, produced by Nippon Denshoku Industries Co., Ltd.)

A solution of 30 wt % sample in N-methyl-2-pyrrolidone, and N-methyl-2-pyrrolidone (a solvent) as a blank were separately subjected to measurement using the transparent color number measurement device. The value obtained by deducting the color number of the solvent from the color number of the sample solution is considered to be the color number of the sample.

Example 1

Dimethyl terephthalate (200 g) and 5% ruthenium/alumina catalyst (3 g) as a catalyst were placed in a 500-ml autoclave provided with an electric, magnetic stirring device. After the system was purged with hydrogen, the reaction was performed at a reaction temperature of 150° C. under a hydrogen pressure of 3 MPa for 5 hours. After cooling, the catalyst was filtered off, and 201 g of dimethyl 1,4-cyclohexanedicarboxylate was obtained. The obtained dimethyl 1,4-cyclohexanedicarboxylate was subjected to gas chromatographic analysis to find that the purity was 98.5%, and that 0.4% of methyl cyclohexanecarboxylate and 0.7% of methyl 4-methylcyclohexanecarboxylate were contained as impurities.

Subsequently, 200 g of the obtained dimethyl 1,4-cyclohexanedicarboxylate, 336 g of ion exchanged water, and 4 g of hydrochloric acid as a catalyst were placed in a 1-L four-necked glass flask equipped with a stirring device, a thermometer, a decanter, and a condenser tube; and the reaction was performed for 11 hours at a reaction temperature of 100° C. while adjusting the distillate amount such that the ion exchanged water was added to the reaction system at a liquid space velocity of 0.5/h. The reaction solution was subjected to gas chromatographic analysis to find that about a trace amount of dimethyl 1,4-cyclohexanedicarboxylate and 0.25% of monomethyl 1,4-cyclohexanedicarboxylate were contained. The obtained reaction solution was gradually cooled to 10° C. over 18 hours, after which the precipitated crystals were filtered off, and the crystals were washed with ion exchanged water having a temperature of 10° C.

Then, the wet crystals were dried at 0.65 kPa at 100° C. for 5 hours in a desiccator that can dry wet crystals while slowly stirring. After the drying, crushing (medium crushing to coarse crushing) was performed using a simple compact grinder to thus obtain 160 g of the target powdery 1,4-cyclohexanedicarboxylic acid (yield: 93%).

The obtained powdery 1,4-cyclohexanedicarboxylic acid was subjected to pretreatment and gas chromatographic analysis to find that the purity was 99.5%.

As to impurities, the total content of dimethyl terephthalate, monomethyl terephthalate, and terephthalic acid, was 0.03%. The cyclohexanecarboxylic acid content was 0.02%, the methyl cyclohexanecarboxylate content was below the detection limit, the 4-methylcyclohexanecarboxylic acid content was 0.05%, the methyl 4-methylcyclohexanecarboxylate content was below the detection limit, and the monomethyl 1,4-cyclohexanedicarboxylate content was 0.04%.

According to the results of the metal analysis, the sodium content was 8 ppm, and the iron content was 0.03 ppm. The water content was 0.03 wt %.

The evaluation of powder properties found that the aerated bulk density was 0.57 g/cm$^3$, the packed bulk density was 0.69 g/cm$^3$, and the compressibility was 17.4%. As for the particle size distributions (on a volume basis), $D_{10}$ was 35 μm, $D_{50}$ was 89 μm, and $D_{90}$ was 274 μm. The average particle size was 100 μm. The angle of repose was 40 degrees, and the dispersion percentage was 25%.

Sixty grams of the obtained powdery 1,4-cyclohexanedicarboxylic acid was placed in a 225-mL mayonnaise bottle, and the flowing state of the powder was visually observed by tilting the bottle. The powder flowed entirely smoothly, indicating that the powder flowability was excellent.

The cis:trans ratio in the 1,4-cyclohexanedicarboxylic acid was 81:19. The color number was 4, the melting point was 168.8° C., and a single peak was observed.

Example 2

1,4-Cyclohexanedicarboxylic acid (156 g) was obtained (yield: 91%) as in Example 1, except that the liquid space velocity was adjusted to 0.1/h, and the reaction time was adjusted to 18 hours.

According to the results of the metal analysis, the sodium content was 8 ppm, and the iron content was 0.03 ppm. The water content was 0.03 wt %.

As to impurities, the total content of dimethyl terephthalate, monomethyl terephthalate, and terephthalic acid, was 0.03%. Further, the cyclohexanecarboxylic acid content was 0.03%, the methyl cyclohexanecarboxylate content was below the detection limit, the 4-methylcyclohexanecarboxylic acid content was 0.05%, the methyl 4-methylcyclohexanecarboxylate content was below the detection limit, and the monomethyl 1,4-cyclohexanedicarboxylate content was 0.04%.

The evaluation of powder properties found that the aerated bulk density was 0.63 g/cm$^3$, the packed bulk density was 0.77 g/cm$^3$, and the compressibility was 18.2%. As for the particle size distributions (on a volume basis), $D_{10}$ was 15 µm, $D_{50}$ was 72 µm, and $D_{90}$ was 313 µm. The average particle size was 75 µm. The angle of repose was 40 degrees, and the dispersion percentage was 20%.

The cis:trans ratio in the 1,4-cyclohexanedicarboxylic acid was 77:23. The color number was 4, the melting point was 168.3° C., and a single peak was observed.

As in Example 1, 60 g of the obtained powdery 1,4-cyclohexanedicarboxylic acid was placed in a 225-mL mayonnaise bottle, and the flowing state of the powder was visually observed by tilting the bottle. The powder flowed entirely smoothly, indicating that the powder flowability was excellent.

Example 3

1,4-Cyclohexanedicarboxylic acid (159 g) was obtained (yield: 92%) as in Example 1, except that the liquid space velocity was adjusted to 0.2/h, and the reaction time to 18 hours. Table 1 shows the measurement results of the obtained powder.

Comparative Example 1

One hundred and forty grams of dimethyl 1,4-cyclohexanedicarboxylate with 98.5% purity (the 4-methylcyclohexanecarboxylic acid content: 0.8 wt %), 360 g of ion exchanged water, and 30 g of sodium hydroxide were placed in a 1-L four-necked glass flask equipped with a stirring device, a thermometer, and a condenser tube, and the reaction was performed at reflux for 2 hours at a reaction temperature of 100° C. to thus obtain a reaction solution of the disodium salt of 1,4-cyclohexanedicarboxylic acid.

About 67 mL of concentrated hydrochloric acid was added at 10° C. to the obtained reaction solution dropwise to allow 1,4-cyclohexanedicarboxylic acid to precipitate. The precipitated crystals were filtered off, and the crystals were sufficiently washed with ion exchanged water having a temperature of 10° C. Subsequently, drying was performed at 0.65 kPa at 100° C. for 3 hours to thus obtain 81 g of 1,4-cyclohexanedicarboxylic acid (yield: 68%).

The obtained 1,4-cyclohexanedicarboxylic acid was subjected to pretreatment and gas chromatographic analysis to find that the purity was 99.3%, the total content of dimethyl terephthalate, monomethyl terephthalate, and terephthalic acid was 0.2%, and the 4-methylcyclohexanecarboxylic acid content was 0.4%.

According to the results of the metal analysis, the sodium content was 60 ppm, and the iron content was 0.03 ppm. The water content was 0.04% of the weight.

The evaluation of powder properties found that the aerated bulk density was 0.49 g/cm³, the packed bulk density was 0.71 g/cm³, and the compressibility was 31.7%. As for the particle size distributions (on a volume basis), $D_{10}$ was 12 µm, $D_{50}$ was 36 µm, and $D_{90}$ was 83 µm. The average particle size was 32 µm. The angle of repose was 47 degrees, and the dispersion percentage was 11%.

The cis:trans ratio in the 1,4-cyclohexanedicarboxylic acid was 80:20. The color number was 4. The melting point was 169.4° C., and in addition to its endothermic peak, two small endothermic peaks were observed at the low-temperature side.

As in Example 1, 60 g of the obtained powdery 1,4-cyclohexanedicarboxylic acid was placed in a 225-mL mayonnaise bottle, and the flowing state of the powder was visually observed by tilting the bottle. The powder adhered to the mayonnaise bottle, indicating that the powder flowability was poor.

Comparative Example 2

One hundred and forty grams of dimethyl 1,4-cyclohexanedicarboxylate with 98.5% purity, 360 g of ion exchanged water, and 4.2 g of sulfuric acid were placed in a 1-L four-necked glass flask equipped with a stirring device, a thermometer, a decanter, and a condenser tube; and the reaction was performed for 10 hours at a reaction temperature of 100° C., while adjusting the distillate amount such that the liquid space velocity was 0.13/h.

The obtained reaction solution was gradually cooled to 10° C. over 4 hours, after which the precipitated crystals were filtered off, and the crystals were washed with ion exchanged water having a temperature of 10° C. Subsequently, drying was performed at 0.65 kPa at 100° C. for 3 hours while being allowed to stand, and 1,4-cyclohexanedicarboxylic acid was obtained. The purity was 99.8%. Due to the occurrence of blocking, the powder properties of the obtained crystals could not be measured. Therefore, Table 1 shows the results as being "unmeasurable."

TABLE 1

| | | Ex. 1 | Ex. 2 | Ex. 3 | Comp. Ex. 1 | Comp. Ex. 2 |
|---|---|---|---|---|---|---|
| Target product (%: GC simple area percentage) | 1,4-cyclohexanedicarboxylic acid | 99.5 | 99.5 | 99.5 | 99.3 | 99.8 |
| Impurity content (%: GC simple area percentage) | Total of dimethyl terephthalate, monomethyl terephthalate, and terephthalic acid | 0.03 | 0.03 | 0.03 | 0.2 | 0.02 |
| | Cyclohexanecarboxylic acid | 0.02 | 0.03 | 0.02 | 0.02 | 0.01 |
| | Methyl cyclohexanecarboxylate | below detection limit | below detection limit | below detection limit | below detection limit | below detection limit |
| | 4-Methyl cyclohexanecarboxylic acid | 0.05 | 0.05 | 0.07 | 0.4 | 0.05 |
| | Methyl 4-methylcyclohexanecarboxylate | below detection limit | below detection limit | below detection limit | below detection limit | below detection limit |
| | Monomethyl 1,4-cyclohexanedicarboxylate | 0.04 | 0.04 | 0.06 | below detection limit | 0.03 |
| Metal content (ppm) | Sodium | 8 | 8 | 8 | 60 | 2 |
| | Iron | 0.03 | 0.03 | 0.03 | 0.03 | 0.03 |
| Water content (wt %) | | 0.03 | 0.03 | 0.03 | 0.04 | 0.03 |
| Powder properties | Aerated bulk density (g/cm³) | 0.57 | 0.63 | 0.68 | 0.49 | Unmeasurable |
| | Packed bulk density (g/cm³) | 0.69 | 0.77 | 0.80 | 0.71 | Unmeasurable |
| | Compressibility (%) | 17.4 | 18.2 | 15.3 | 31.7 | Unmeasurable |
| | Particle size distribution (volume basis) (µm) $D_{10}$ | 35 | 15 | 19 | 12 | Unmeasurable |
| | $D_{50}$ | 89 | 72 | 106 | 36 | Unmeasurable |

TABLE 1-continued

|  | Ex. 1 | Ex. 2 | Ex. 3 | Comp. Ex. 1 | Comp. Ex. 2 |
|---|---|---|---|---|---|
| $D_{90}$ | 274 | 313 | 665 | 83 | Unmeasurable |
| Average particle size (μm) | 100 | 75 | 109 | 32 | Unmeasurable |
| Angle of repose (degree) | 40 | 40 | 41 | 47 | Unmeasurable |
| Dispersion percentage (%) | 25 | 20 | 20 | 11 | Unmeasurable |
| Color number (Hazen) | 4 | 4 | 2 | 4 | 4 |
| Melting point (° C.) | 168.8 | 168.3 | 168.1 | 169.4 | 168.8 |

INDUSTRIAL APPLICABILITY

The powdery 1,4-cyclohexanedicarboxylic acid according to the present invention is high-purity 1,4-cyclohexanedicarboxylic acid having excellent powder flowability and excellent physical properties with a reduced amount of impurities. The powdery 1,4-cyclohexanedicarboxylic acid according to the present invention having such properties contributes to an improvement in workability since it is easily charged or easily handled during operation, and can also be used as a useful starting material of medicinal drugs, synthetic resins, synthetic fibers, and dyes.

The invention claimed is:

1. Powdery 1,4-cyclohexanedicarboxylic acid having:
    particle size distributions (volume basis) such that $D_{10}$ is within a range of 5 to 55 μm, $D_{50}$ is within a range of 40 to 200 μm, and $D_{90}$ is within a range of 170 to 800 μm;
    an aerated bulk density of 0.4 to 0.8 g/cm$^3$;
    a packed bulk density of 0.5 to 1.0 g/cm$^3$; and
    a compressibility of 10 to 23%.

2. The powdery 1,4-cyclohexanedicarboxylic acid according to claim 1, wherein the cis:trans ratio in the 1,4-cyclohexanedicarboxylic acid is 50:50 to 90:10.

3. The powdery 1,4-cyclohexanedicarboxylic acid according to claim 1, containing dialkyl (C1-C4) terephthalate, monoalkyl (C1-C4) terephthalate, and terephthalic acid in a total amount of 0.2% or less in the powdery 1,4-cyclohexanedicarboxylic acid.

4. The powdery 1,4-cyclohexanedicarboxylic acid according to claim 1,
    wherein the powdery 1,4-cyclohexanedicarboxylic acid satisfies at least one member selected from the group consisting of the following (a) to (e):
    (a) containing alkyl (C1-C4) cyclohexanecarboxylate in an amount of 0.1% or less;
    (b) containing cyclohexanecarboxylic acid in an amount of 0.1% or less;
    (c) containing alkyl (C1-C4) 4-methylcyclohexanecarboxylate in an amount of 0.1% or less;
    (d) containing 4-methylcyclohexanecarboxylic acid in an amount of 0.3% or less; and
    (e) containing monoalkyl (C1-C4) 1,4-cyclohexanedicarboxylate in an amount of 0.5% or less,
    and also satisfies at least one member selected from the group consisting of the following (i) to (iii):
    (i) containing one or more alkali metals in an amount of 20 ppm or less (weight basis);
    (ii) containing water in an amount of 0.1 wt % or less; and
    (iii) having a color number (Hazen) of 50 or less.

5. A method for producing powdery 1,4-cyclohexanedicarboxylic acid of claim 1, the method comprising the steps of:
    (1) subjecting dialkyl (C1-C4) terephthalate to nuclear hydrogenation to obtain dialkyl (C1-C4) 1,4-cyclohexanedicarboxylate;
    (2) hydrolyzing the dialkyl (C1-C4) 1,4-cyclohexanedicarboxylate obtained in step (1) in the presence of an acid catalyst in the presence of water or a water-containing solvent to obtain 1,4-cyclohexanedicarboxylic acid;
    (3) crystallizing the 1,4-cyclohexanedicarboxylic acid obtained in step (2);
    (4) subjecting the crystals of the 1,4-cyclohexanedicarboxylic acid obtained in step (3) to solid-liquid separation; and
    (5) drying, drying and granulating, or drying and crushing wet crystals of the 1,4-cyclohexanedicarboxylic acid obtained in step (4), wherein the step of drying the wet crystals in step (5) is a step of drying the wet crystals while stirring; and optionally
    (6) classifying a powder of the 1,4-cyclohexanedicarboxylic acid obtained in step (5).

6. Powdery 1,4-cyclohexanedicarboxylic acid produced by a method comprising the steps of:
    (1) subjecting dialkyl (C1-C4) terephthalate to nuclear hydrogenation to obtain dialkyl (C1-C4) 1,4-cyclohexanedicarboxylate;
    (2) hydrolyzing the dialkyl (C1-C4) 1,4-cyclohexanedicarboxylate obtained in step (1) in the presence of an acid catalyst in the presence of water or a water-containing solvent to obtain 1,4-cyclohexanedicarboxylic acid;
    (3) crystallizing the 1,4-cyclohexanedicarboxylic acid obtained in step (2);
    (4) subjecting crystals of the 1,4-cyclohexanedicarboxylic acid obtained in step (3) to solid-liquid separation; and
    (5) drying, drying and granulating, or drying and crushing wet crystals of the 1,4-cyclohexanedicarboxylic acid obtained in step (4), wherein the step of drying the wet crystals in step (5) is a step of drying the wet crystals while stirring; and optionally
    (6) classifying a powder of the 1,4-cyclohexanedicarboxylic acid obtained in step (5).

7. The powdery 1,4-cyclohexanedicarboxylic acid according to claim 1, which is produced by a method comprising the steps of:
    (1) subjecting dialkyl (C1-C4) terephthalate to nuclear hydrogenation to obtain dialkyl (C1-C4) 1,4-cyclohexanedicarboxylate;
    (2) hydrolyzing the dialkyl (C1-C4) 1,4-cyclohexanedicarboxylate obtained in step (1) in the presence of an acid catalyst in the presence of water or a water-containing solvent to obtain 1,4-cyclohexanedicarboxylic acid;
    (3) crystallizing the 1,4-cyclohexanedicarboxylic acid obtained in step (2);
    (4) subjecting the crystals of the 1,4-cyclohexanedicarboxylic acid obtained in step (3) to solid-liquid separation; and
    (5) drying, drying and granulating, or drying and crushing wet crystals of the 1,4-cyclohexanedicarboxylic acid obtained in step (4), wherein the step of drying the wet crystals in step (5) is a step of drying the wet crystals while stirring; and optionally (6) classifying a powder of the 1,4-cyclohexanedicarboxylic acid obtained in step (5).

\* \* \* \* \*